(12) United States Patent
Kautzsch et al.

(10) Patent No.: US 9,136,136 B2
(45) Date of Patent: Sep. 15, 2015

(54) METHOD AND STRUCTURE FOR CREATING CAVITIES WITH EXTREME ASPECT RATIOS

(71) Applicant: Infineon Technologies Dresden GmbH, Dresden (DE)

(72) Inventors: Thoralf Kautzsch, Dresden (DE); Heiko Fröhlich, Radebeul (DE); Mirko Vogt, Dresden (DE); Maik Stegemann, Pesterwitz (DE)

(73) Assignee: Infineon Technologies Dresden GmbH, Dresden (DE)

( * ) Notice: Subject to any disclaimer, the term of this patent is extended or adjusted under 35 U.S.C. 154(b) by 0 days.

(21) Appl. No.: 14/031,694

(22) Filed: Sep. 19, 2013

(65) Prior Publication Data

US 2015/0079787 A1  Mar. 19, 2015

(51) Int. Cl.
| H01L 21/306 | (2006.01) |
| G01N 33/487 | (2006.01) |
| G01N 27/414 | (2006.01) |
| G01N 27/447 | (2006.01) |
| H01L 29/06 | (2006.01) |

(52) U.S. Cl.
CPC ........ *H01L 21/30604* (2013.01); *G01N 27/414* (2013.01); *G01N 27/4473* (2013.01); *G01N 33/48721* (2013.01); *H01L 29/06* (2013.01)

(58) Field of Classification Search
None
See application file for complete search history.

(56) References Cited

U.S. PATENT DOCUMENTS

| 4,317,126 A | 2/1982 | Gragg, Jr. |
| 4,966,663 A | 10/1990 | Mauger |
| 5,129,981 A | 7/1992 | Wang |
| 5,167,778 A | 12/1992 | Kaneko |
| 5,332,469 A | 7/1994 | Mastrangelo |
| 5,445,718 A | 8/1995 | Wang |
| 5,501,893 A | 3/1996 | Laermer |
| 5,719,073 A | 2/1998 | Shaw |
| 5,968,336 A | 10/1999 | Rolfson |
| 6,006,607 A | 12/1999 | Bryzek et al. |

(Continued)

FOREIGN PATENT DOCUMENTS

| CN | 101267689 A | 9/2008 |
| CN | 101479185 A | 7/2009 |

(Continued)

OTHER PUBLICATIONS

Application and File History for U.S. Appl. No. 13/032,334, filed Feb. 22, 2011, inventors Winkler et al.

(Continued)

*Primary Examiner* — Duy Deo
(74) *Attorney, Agent, or Firm* — Eschweiler & Associates, LLC

(57) ABSTRACT

Embodiments relate to structures, systems and methods for more efficiently and effectively etching sacrificial and other layers in substrates and other structures. In embodiments, a substrate in which a sacrificial layer is to be removed to, e.g., form a cavity comprises an etch dispersion system comprising a trench, channel or other structure in which etch gas or another suitable gas, fluid or substance can flow to penetrate the substrate and remove the sacrificial layer. The trench, channel or other structure can be implemented along with openings or other apertures formed in the substrate, such as proximate one or more edges of the substrate, to even more quickly disperse etch gas or some other substance within the substrate.

9 Claims, 3 Drawing Sheets

(56) References Cited

U.S. PATENT DOCUMENTS

| | | | |
|---|---|---|---|
| 6,093,330 | A | 7/2000 | Chong |
| 6,122,964 | A | 9/2000 | Mohaupt et al. |
| 6,357,299 | B1 | 3/2002 | Aigner |
| 6,379,990 | B1 | 4/2002 | Mueller et al. |
| 6,531,068 | B2 | 3/2003 | Laermer |
| 6,653,702 | B2 | 11/2003 | Ishio et al. |
| 6,662,663 | B2 | 12/2003 | Chen |
| 7,288,824 | B2 | 10/2007 | Partridge et al. |
| 7,300,854 | B2 | 11/2007 | Benzel et al. |
| 7,629,657 | B2 | 12/2009 | Partridge et al. |
| 7,833,405 | B2 | 11/2010 | Benzel et al. |
| 7,859,067 | B2 | 12/2010 | Partridge et al. |
| 8,421,169 | B2 | 4/2013 | Kittilsland et al. |
| 2002/0020053 | A1 | 2/2002 | Fonash |
| 2002/0086456 | A1 | 7/2002 | Cunningham |
| 2002/0086551 | A1 | 7/2002 | Beetz |
| 2002/0137348 | A1 | 9/2002 | Micak |
| 2002/0148807 | A1 | 10/2002 | Zhao |
| 2002/0185469 | A1 | 12/2002 | Podlesnik |
| 2004/0067346 | A1 | 4/2004 | Hofmann |
| 2005/0176198 | A1 | 8/2005 | Kudelka |
| 2005/0260783 | A1 | 11/2005 | Lutz et al. |
| 2006/0231521 | A1 | 10/2006 | Chilcott |
| 2006/0292877 | A1 | 12/2006 | Lake |
| 2007/0072428 | A1 | 3/2007 | Chilcott |
| 2007/0077727 | A1 | 4/2007 | Huang |
| 2007/0170528 | A1 | 7/2007 | Partridge et al. |
| 2008/0061029 | A1 | 3/2008 | Lai |
| 2008/0237756 | A1 | 10/2008 | Partridge et al. |
| 2008/0293250 | A1 | 11/2008 | Dussart |
| 2009/0007681 | A1 | 1/2009 | Stewart |
| 2009/0309175 | A1 | 12/2009 | Partridge |
| 2010/0001615 | A1* | 1/2010 | Steeneken et al. ............. 310/300 |
| 2010/0003143 | A1* | 1/2010 | Toonder et al. ................. 417/53 |
| 2010/0147070 | A1 | 6/2010 | Jun |
| 2010/0313660 | A1 | 12/2010 | Nishikage |
| 2011/0132872 | A1 | 6/2011 | Van De Sande |
| 2011/0207323 | A1 | 8/2011 | Ditizio |
| 2011/0227558 | A1* | 9/2011 | Mannion et al. .............. 324/71.1 |
| 2012/0126346 | A1 | 5/2012 | Hoechst |
| 2012/0205753 | A1 | 8/2012 | Adams |
| 2012/0211805 | A1 | 8/2012 | Winkler et al. |
| 2012/0235254 | A1 | 9/2012 | Mohanakrishnaswamy et al. |
| 2012/0264249 | A1 | 10/2012 | Kundalgurki |
| 2013/0270658 | A1 | 10/2013 | Behrendt et al. |
| 2014/0252422 | A1 | 9/2014 | Winkler et al. |
| 2015/0001665 | A1 | 1/2015 | Kautzsch |

FOREIGN PATENT DOCUMENTS

| | | |
|---|---|---|
| DE | 4000496 A1 | 2/1991 |
| DE | 19700290 | 7/1998 |
| WO | WO2007087021 | 8/2007 |
| WO | 2010052684 A2 | 5/2010 |

OTHER PUBLICATIONS

Application and File History for U.S. Patent Application No. 14/281,251, filed May 19, 2014, inventors Winkler et al.

Rogers, T., "*Selective Anodization Using Masked Deep Ion Implantation*", J. Micromech. Micreng. 3 (1993), pp. 146-148.

Prime Faraday Technology Watch, ISBN 1-84402-020-7, "*An Introduction to MEMS (Micro-electromechanical Systems)*", Jan. 2002, 56 pgs.

Semiconductor Materials Product Guide, MEMC at p. 5 downloaded from http://sunedisonsilicon.com/assets/file/products/semiconductor/SunEdison_Semi conductor_Brochure.pdf. Aug. 29, 2013.

Definition of "Standard", download from http://www.thefreedictionary.com/standard, Sep. 2, 2013.

Bosch, Research Info, *Revolution Under the Hood*, http://researchinfo.bosch.com, Issue Jan. 2003, 4 pages.

Ernst, Dr, Peter, "*MEMS @ Bosch: Automotive Applications and Beyond*". Jun. 4, 2007. 9 pages.

Vigna, Benedetto, "*Making Mems: A Short Guide*". EE Times, Oct. 7, 2008. 2 pages.

LPS001WP, MEMS pressure sensor 300-1100 mbar absolute digital output barometer, Doc ID18171, Rev. 1. Nov. 2010. pp. 1-30.

SiTime: It's About Time, "*SiTime's MEMS First™ Process*", SiT-AN20001 Rev.1.7, Feb. 17, 2009, pp. 1-6.

German Office Action, Application No. 102012202643.6, mailed Oct. 23, 2014, 7 pages.

Silicon Designs, "Data Sheet 2210 1-Axis Accelerometer", downloaded from http://www.silicondesigns.com/ds/ds2210.html, accessed Jan. 31, 2015, 2 pages.

\* cited by examiner

METHOD AND STRUCTURE FOR CREATING CAVITIES WITH EXTREME ASPECT RATIOS

TECHNICAL FIELD

The invention relates generally to semiconductors, and more particularly to semiconductor substrates and structures having cavities formed therein and methods for forming those cavities.

BACKGROUND

Micromechanical devices, such as sensors and other components, often comprise moveable elements disposed in or adjacent to cavities within a substrate or other structure. For example, a micro-electromechanical system (MEMS) sensor, such as for sensing pressure, acceleration or some other quantity can have a membrane or mass element disposed in or adjacent to a cavity.

Use of existing CMOS process techniques to form these and other sensors and devices, including those which may incorporate new technology aspects and/or are of increasingly reduced dimensions, can be advantageous with respect to cost and complexity. At the same time, challenges can exist in successfully forming the sensors and devices, both with respect to feature dimensions and such that the membranes, mass elements and other moveable elements are fully formed and separated from adjacent structures such that they can move as designed and the sensor or other device can function properly. A common problem is that moveable elements stick to or are not fully separated from the wall of a cavity in which they are formed, resulting in a nonfunctioning device. Conventional systems and methods for forming these small-scale sensors and devices with sufficient separation of components, however, can be expensive, time-consuming (e.g., having limited etch speed) and still limited by certain dimensions and feature sizes.

SUMMARY

Embodiments relate to etch dispersion systems, such as for substrates and other structures, that facilitate efficient and effective removal of sacrificial material within a relatively large area of a substrate.

In an embodiment, an etch dispersion system formed in a substrate comprises at least one dispersion aperture formed in the substrate and configured to provide access to a sacrificial layer of the substrate by an etch material; and at least one dispersion channel formed in the substrate proximate the sacrificial layer and configured to facilitate dispersion of the etch material within the substrate.

In an embodiment, a method of removing a sacrificial layer in a substrate comprises applying an etch material to the substrate; accessing the sacrificial layer by the etch material via at least one aperture formed in the substrate; removing a portion of the sacrificial layer by the etch material to access at least one channel formed in the substrate; and removing a remaining portion of the sacrificial layer by the etch material via the at least one channel and the at least one aperture.

In an embodiment, a method of removing a sacrificial layer in a substrate comprises applying an etch material to the substrate; accessing the sacrificial layer by the etch material via at least one aperture formed in a surface of the substrate and at least one channel formed within the substrate; and removing the sacrificial layer by the etch material via the at least one channel and the at least one aperture.

BRIEF DESCRIPTION OF THE DRAWINGS

The invention may be more completely understood in consideration of the following detailed description of various embodiments of the invention in connection with the accompanying drawings, in which.

Figure 1A:
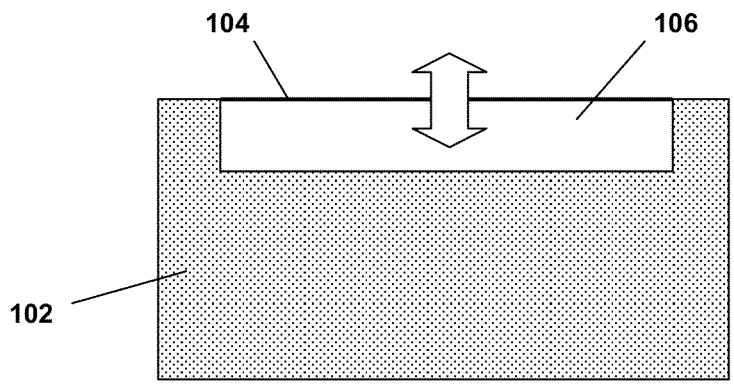
FIG. 1A is side cross-sectional view of a block diagram of a substrate comprising a cavity and membrane according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Embodiments relate to structures, systems and methods for more efficiently and effectively etching sacrificial and other layers in substrates and other structures. In embodiments, a substrate in which a sacrificial layer is to be removed to, e.g., form a cavity comprises an etch dispersion system comprising a trench, channel or other structure in which etch gas or another suitable gas, fluid or substance can flow to penetrate the substrate and remove the sacrificial layer. The trench, channel or other structure can be implemented along with openings or other apertures formed in the substrate, such as proximate one or more edges of the substrate, to even more quickly disperse etch gas or some other substance within the substrate.

Figure 1B:
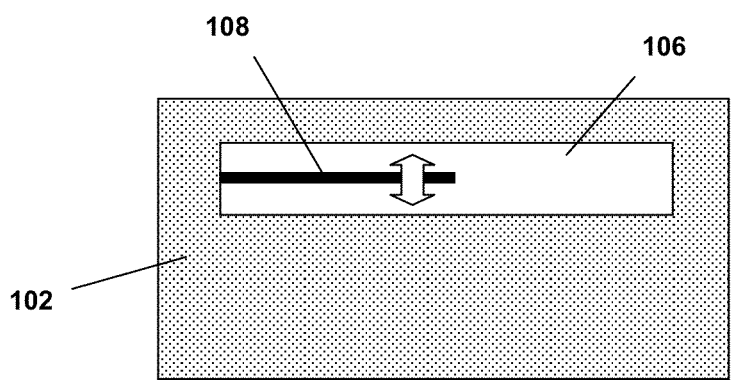
FIG. 1B is side cross-sectional view of a block diagram of a substrate comprising a cavity and a beam according to an embodiment.

FIGS. 1A and 1B depict example substrates 102 comprising moveable elements. The depictions in FIGS. 1A and 1B are simplified, and other structures, e.g., electrodes, which generally would be present in such a substrate 102 or device comprising substrate 102 are not shown. Additionally, the portion of substrate 102 depicted in either FIG. 1A or 1B may be an intermediary portion of a larger substrate, structure or device, such that other layers or elements may be arranged on top of, under, around or adjacent part or all of substrate 102 as depicted. Thus, FIGS. 1A and 1B are provided merely to illustrate simplified examples of substrates and structures which may be applicable to embodiments and examples discussed herein. Moreover, the use of the term "substrate" herein throughout is for convenience, as the substrate can comprise some other structure, substructure, device or component in various embodiments.

In FIG. 1A, substrate 102 comprises a membrane 104 proximate a cavity 106 such that membrane 104 can flex up or down (as depicted on the page), e.g., become generally more convex or concave, in response to, e.g., pressure or acceleration. In FIG. 1B, substrate 102 comprises a cantilevered beam 108, disposed in cavity 106, which can bend or flex up and down in response to, e.g., acceleration or capacitance.

In both FIGS. 1A and 1B, cavity 106 and either membrane 104 or beam 108 are formed from or within substrate 102. Both membrane 104 and beam 108 must be sufficiently separated from the surrounding structures so that each can move and operate as intended. In embodiments, material of substrate 102 is etched or otherwise removed from substrate 102, thereby forming cavity 106, in order to accomplish this. The material of substrate 102 can vary in embodiments, and correspondingly other materials including the etch gas or fluid. In one embodiment, a sacrificial layer of substrate 102 comprises carbon and the etching gas comprises ozone or another suitable material. These materials are merely examples, however, as those skilled in the art will appreciate that virtually any suitable combinations of materials (e.g., a sacrificial layer material and an etch material, such as a gas, fluid or other suitable material, capable of sufficiently etching the material comprising the sacrificial layer) can be used in the context of embodiments discussed herein.

Figure 2A:
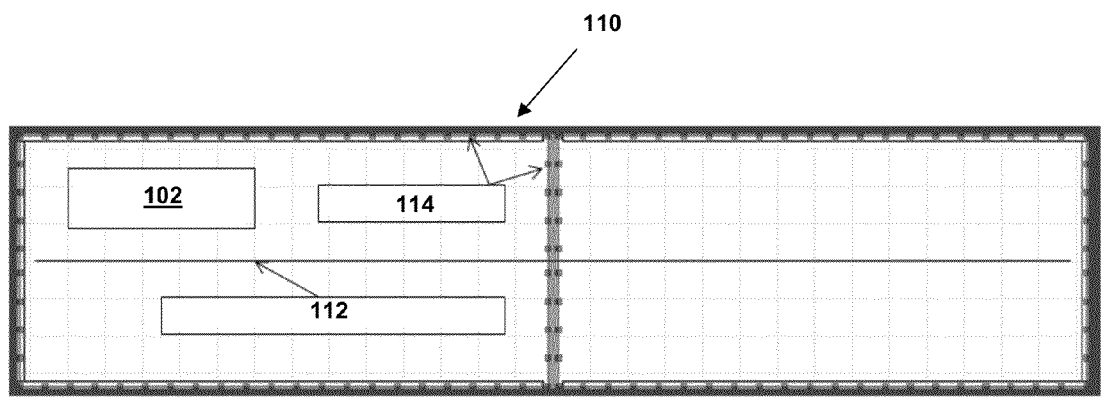
FIG. 2A is a top view of a substrate comprising an etch dispersion system according to an embodiment.
Figure 2B:
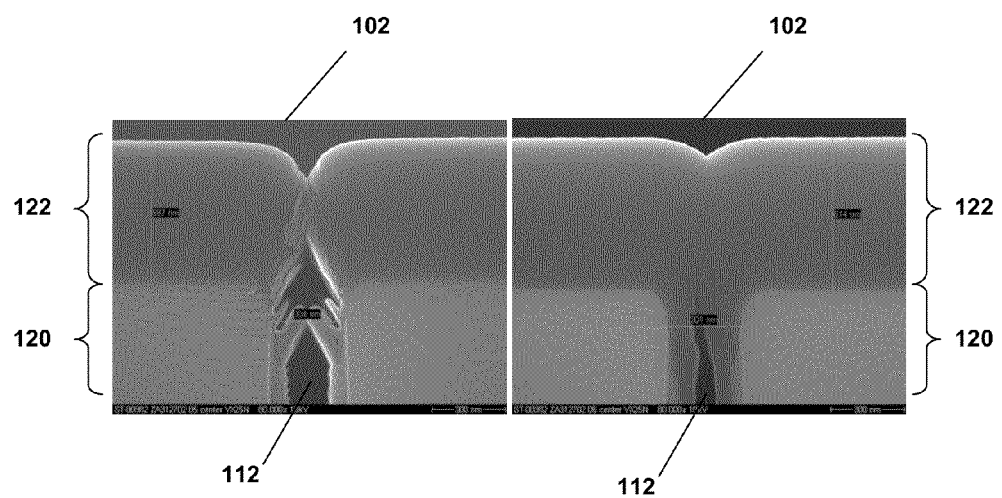
FIG. 2B is a side cross-sectional view of channels formed in substrates according to an embodiment.
Figure 2C:
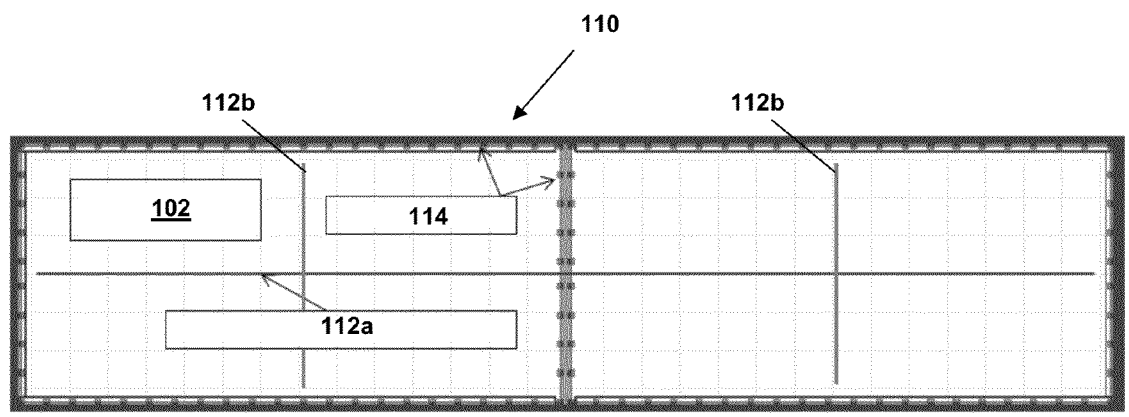
FIG. 2C is a top view of a substrate comprising an etch dispersion system according to an embodiment.

In embodiments, and also referring to FIG. 2, the etching of substrate 102 to form cavity 106 or some other void, aperture or structure is accomplished by implementing an etch dispersion system 110 in substrate 102. As depicted in the embodiment of FIG. 2, etch dispersion system 110 comprises at least one trench or channel 112 and a plurality of apertures 114 formed in substrate 102, which in one example embodiment comprises a silicon substrate, a carbon sacrificial layer formed on the silicon substrate, and a nitride cover layer formed on the carbon sacrificial layer. The nitride cover layer is that which is visible as the top layer in the top view of FIG. 2, with channel 112 formed in the silicon layer but depicted as visible in FIG. 2A for purposes of illustration. Referring also to FIG. 2B, photos of a test substrate 102 are shown, with channel 112 formed in silicon layer 120 and a carbon sacrificial layer 122 subsequently deposited on top (anisotropically on the left, and isotropically on the right) as part of the formation or manufacture of substrate 102. As previously mentioned, virtually any suitable materials and layer structures can be used in other embodiments, as appreciated by those skilled in the art.

Figure 3:
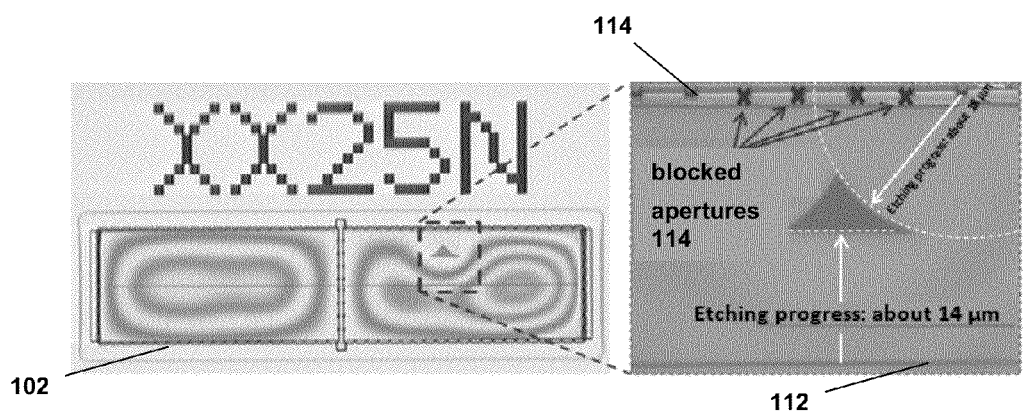
FIG. 3 is a depiction of a test substrate comprising an etch dispersion system according to an embodiment.

Channel 112 extends generally longitudinally within substrate 102, though the placement and configuration of channel 112 can vary in other embodiments and be optimized according to the configuration and dimensions of substrate 102 and/or the cavity or other feature being formed therein. For example, the particular length, width and depth of channel 112 can vary according to a length width and depth of substrate 102 and/or of the cavity or other structure to be formed within substrate 102. In other embodiments, the placement and configuration of channel 112 can be optimized according to the structure or features of substrate 102. In embodiments, for example, channel 112 is less than about 500 nm wide, such as less than about 300 nm wide, for example about 100 nm wide in one embodiment; about 0.5 microns ($\mu$m) to about 10 $\mu$m deep in embodiments; and about 10 $\mu$m to about 100 $\mu$m long in embodiments; though one or more of these dimensions and/or ranges can vary in embodiments according to one or more dimensions or other characteristics of substrate 102 or some other factor. Additionally, the dimensions of different channels on any particular substrate 102 can vary, such that some are larger, smaller, longer, shorter or deeper than others on the same substrate 102. Different sizes can be implemented, e.g., in consideration of dimensions, structure, materials or other characteristics of substrate 102, an etch gas or material used, or some other factor. Moreover, in embodiments a system comprising a plurality of channels 112 can be implemented; for example, in FIG. 2 additional channels or trenches being generally parallel with or perpendicular to channel 112, or at another angle with respect thereto, and/or formed in the same or different surfaces or layers of substrate 102, can be implemented in other embodiments. For example, in one embodiment depicted in FIG. 2C, a primary channel 112a 2 can be formed in substrate 102 along with a plurality of smaller channels 112b. The channels 112a and 112b can interconnect originally or become interconnected via the etching process, and can be formed in the same or different layers, or at the same or different depths, of substrate 102. The density of the channels 112 can depend on the lateral clearance width of the etching process used in embodiments. Referring also to FIG. 3, which will be discussed in more detail below, test results of a structure similar to that depicted in FIG. 2, however, were positive, such that a system 110 having additional components may be not be necessary or desired in various embodiments.

Apertures 114 are arranged around an outer perimeter of substrate 102 as well as along a central portion as depicted in FIG. 2. The size (e.g., diameter and/or depth), relative spacing and number of apertures 114 can vary in embodiments according to a configuration of substrate 102 and/or of the cavity or other structure to be formed within substrate 102. In embodiments apertures 114 are about 100 nm to about 1 $\mu$m in diameter or width and are spaced apart by about 1 $\mu$m to about 20 $\mu$m, though these dimensions and ranges can vary in other embodiments. For example, in some embodiments smaller diameter apertures 114 are spaced more closely together, in other embodiments larger diameter apertures 114 are spaced further apart. In still other embodiments, apertures 114 on any particular substrate 114 can vary in size, such that some are larger or smaller than others. Different sizes can be implemented, e.g., in consideration of dimensions, structure, materials or other characteristics of substrate 102, an etch gas or material used, or some other factor. The placement and arrangement of apertures 114 also can vary in embodiments, with more or fewer apertures 114 arranged in similar or different configurations used in other embodiments. For example, in one embodiment apertures 114 along the central portion of substrate 102 are omitted if, for example, the width or lateral dimension of substrate 102 makes those apertures 114 unnecessary. In other embodiments, fewer but larger apertures 114 are used, or some other aperture-like structure is implemented.

Etch dispersion system 110 enables efficient and effective etching of relatively large areas of substrate 102, such as on the order of square millimeters (mm) in some embodiments, or more or less in other embodiments, by providing way for the etch gas or other material to quickly penetrate to and remove the sacrificial layer. For example, in one embodiment a cavity having a height on the order of about several tens of nanometers (nm) and lateral dimensions on the order of about several hundreds of micrometers ($\mu$m), can be formed using etch dispersion system 110. This can be helpful in many applications, such as next-generation pressure sensors, accelerometers, resonators and other devices, which have large areas to etch but are frequently plagued by the aforementioned challenges related to etch speeds and effectiveness. Many other applications are also possible and are not limited to these or other devices given as examples herein.

In operation, an etching gas, such as ozone, or another suitable substance is applied and penetrates substrate 102 via apertures 114. The etch gas will reach channel 112 once sufficient amounts of the sacrificial layer are reached via apertures 114 (e.g., the apertures most proximate channel 112, such as at the left end and near the center of channel 112 in FIG. 2). Upon reaching channel 112, the gas will spread within channel 112 and begin attacking the sacrificial layer therefrom. If other channels or features are included in any particular etch dispersion system within substrate 102, the etch gas will also reach and disperse within substrate 102 thereby. As the gas penetrates substrate 102 via this etch dispersion system, the gas eventually begins to attach the sacrificial layer material from essentially all sides and from within while still maintaining the nitride or other cover layer (s). Despite its small dimensions, channel 112 enables fast dispersion of the etch gas and efficient etching of the sacrificial layer within substrate 102. Thus, the addition of even one small trench can significantly improve exposure to sacrificial layer area within substrate 102.

Referring to FIG. 3, test results of substrate 102 are depicted. As can be seen in the left portion of substrate 102, the etch gas successfully penetrated to and removed the sacrificial layer. In the right portion of substrate 102, results are depicted in which several of the perimeter apertures 114 were inadvertently blocked or plugged. The penetration of the etch gas via neighboring unblocked apertures 114 and channel 112 can be seen clearly, with the dark triangular portion in the enlarged view of the right portion of substrate 102 being a remnant of the sacrificial layer.

In other embodiments, other configurations of etch dispersion system 110 can be implemented. For example, a plurality of channels can be implemented. Whether a single channel or plurality of channels are used, the channel(s) can be embedded as in FIG. 2, or can be directly coupled to one or more apertures or other features of system 110 or substrate 102 to facilitate efficient and effective etching and removal of sacrificial material. If a plurality of channels are implemented, some or all can be coupled together as a channel system, and/or can be coupled to one or more apertures or embedded, and/or can be arranged in the same or different layers. The particular features and configuration of any system 110 can depend on the sacrificial area, overall dimensions of the substrate or other device, form and/or function of the substrate or other device, or other characteristics appreciated by those skilled in the art. In other words, an advantage of embodiments is the flexibility with respect to design and features of any system 110 such that it can be adapted to and implemented in a wide variety of structures.

Embodiments of etch dispersion systems therefore provide efficient and effective etching of sacrificial and other layers within substrates. These systems enable etch gas or another substance to quickly penetrate into central, hard-to-reach and/or other regions of a substrate via at least one narrow channel. The channel can be implemented with one or more apertures formed in the substrate, and the apertures can be the initial means of penetration into the substrate, with the channel being reached via initial etching through the sacrificial layer which then accelerates dispersion of the etch gas or other substance within the substrate. Even as a secondary penetration means, the etch rate via the channel can be virtually the same as that via the apertures, such as within a few percent in embodiments.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A method of removing a sacrificial layer in a substrate, comprising:
    applying an etch material to the substrate, wherein the substrate comprises at least one pre-existing aperture and at least one pre-existing channel;
    penetrating the substrate with the etch material via the at least one pre-existing aperture formed in the substrate;
    removing a portion of the sacrificial layer by the etch material to reach the at least one pre-existing channel formed in the substrate with the etch material;
    dispersing the etch material via the at least one pre-existing channel formed in the substrate; and
    removing a remaining portion of the sacrificial layer by the etch material via the at least one pre-existing channel and the at least one pre-existing aperture.

2. The method of claim 1, further comprising:
    forming the at least one pre-existing channel in a layer of the substrate proximate the sacrificial layer; and
    forming the at least one pre-existing aperture in the substrate.

3. The method of claim 2, wherein forming the at least one pre-existing channel comprises forming a plurality of channels.

4. The method of claim 2, further comprising depositing at least one layer over the at least one pre-existing channel.

5. The method of claim 4, wherein forming the at least one pre-existing aperture comprises forming the at least one pre-existing aperture in the at least one layer over the at least one pre-existing channel.

6. A method of removing a sacrificial layer in a substrate, comprising:
- applying an etch material to the substrate, wherein the substrate comprises at least one pre-existing aperture formed in a surface of the substrate and at least one pre-existing channel formed within the substrate;
- penetrating the substrate with the etch material via the at least one pre-existing aperture and the at least one pre-existing channel; and
- removing the sacrificial layer by the etch material via the at least one pre-existing channel and the at least one pre-existing aperture.

7. The method of claim 6, further comprising forming the at least one pre-existing aperture and the at least one pre-existing channel in the substrate.

8. The method of claim 7, wherein forming the at least one pre-existing channel further comprises forming a first channel of the at least one pre-existing channel with a width less than about 300 nanometers.

9. The method of claim 6, wherein the penetrating further comprises reaching the at least one pre-existing channel with the etch material via the at least one pre-existing aperture.

\* \* \* \* \*